United States Patent [19]

Kotsanis

[11] 4,447,227
[45] May 8, 1984

[54] MULTI-PURPOSE MEDICAL DEVICES

[75] Inventor: Constantine A. Kotsanis, River Grove, Ill.

[73] Assignee: Endoscopy Surgical Systems, Inc., White Haven, Pa.

[21] Appl. No.: 386,558

[22] Filed: Jun. 9, 1982

[51] Int. Cl.³ .............................................. A61M 25/02
[52] U.S. Cl. ........................................ 604/95; 604/96; 604/101
[58] Field of Search ...................... 604/101, 96, 95, 97, 604/98, 99; 128/207.14, 207.15

[56] References Cited

U.S. PATENT DOCUMENTS

| | | | |
|---|---|---|---|
| 2,470,665 | 5/1949 | Stiehl | 604/96 |
| 2,855,934 | 10/1958 | Daughoday | 604/95 |
| 4,066,070 | 1/1978 | Utsagi | 604/95 X |
| 4,198,981 | 4/1980 | Sinnreich | 604/101 X |
| 4,340,046 | 7/1982 | Cox | 604/96 X |

Primary Examiner—Stephen C. Pellegrino
Attorney, Agent, or Firm—John Kurucz

[57] ABSTRACT

Multi-purpose pneumatic and hydraulic devices suitable for diagnostic and surgical use facilitate surgical procedures as well as enhance patient care and recovery by minimizing trauma, infection and iatrogenic complications. The multi-purpose devices each have at least one medical grade balloon and a stabilizing assembly to enhance positioning and engagement of the balloon in a lumen. The stabilizing assembly can take the form of another medical grade balloon or one or more vacuum responsive members, such as active or passive microsuckers. The multi-purpose device can also be equipped with a self-advancing unit, a bypass circuit, a vacuum retractor, a crusher, a multi-lens system and/or a fiberscope.

9 Claims, 49 Drawing Figures

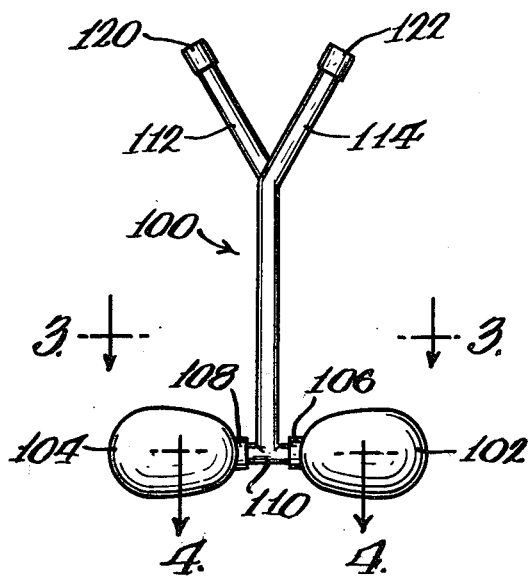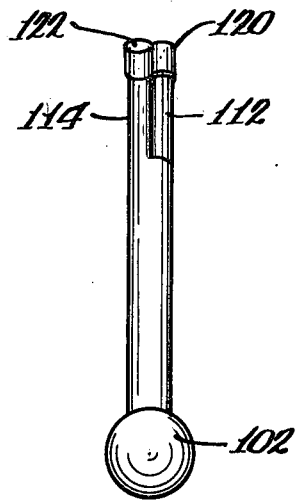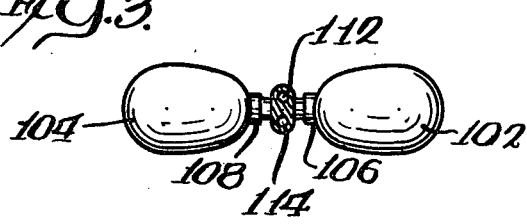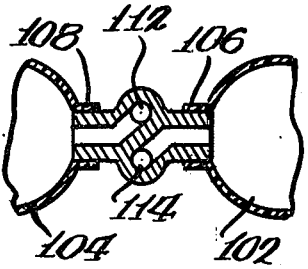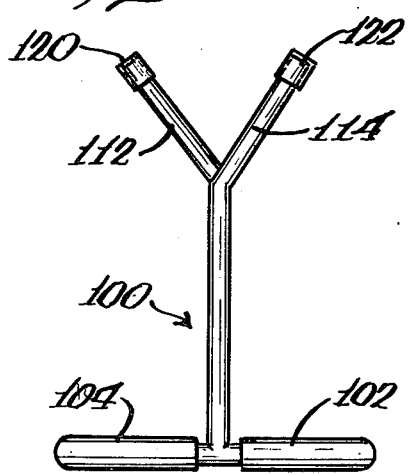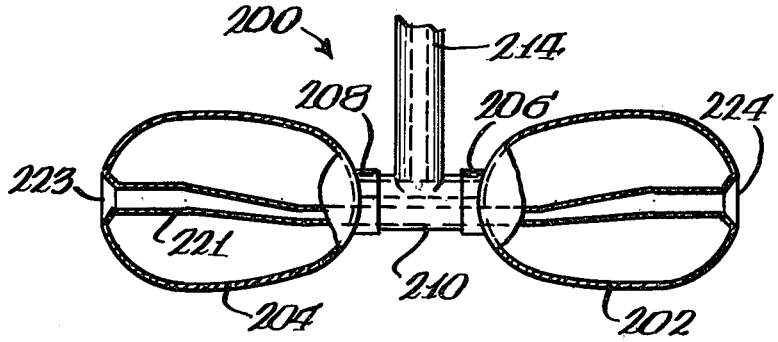

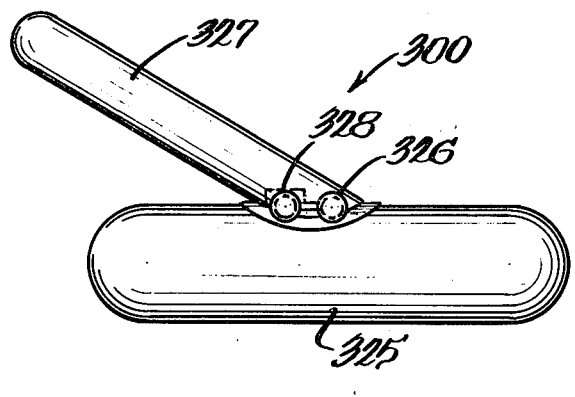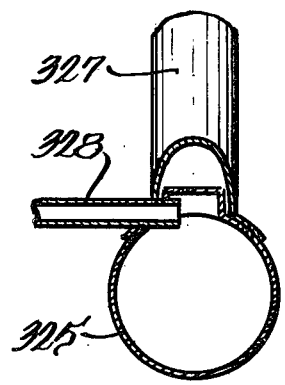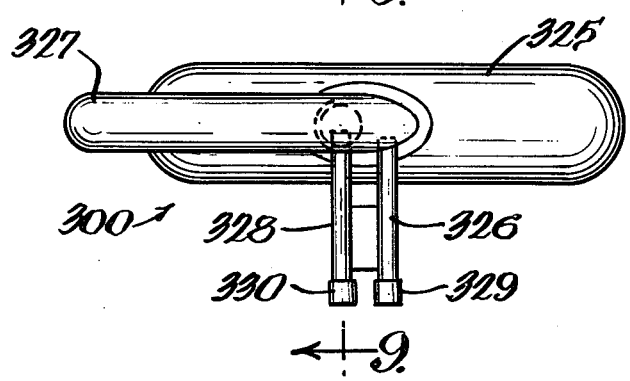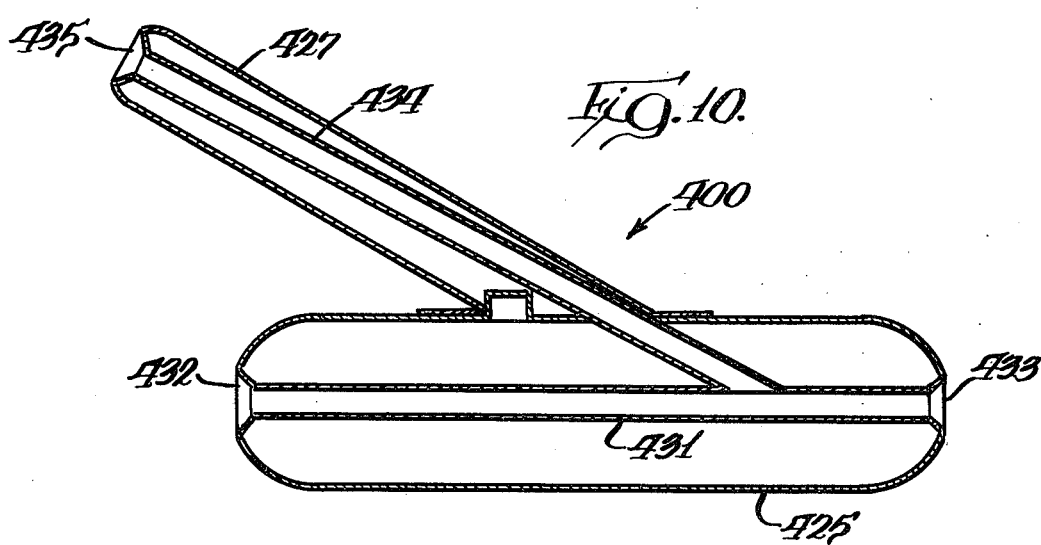

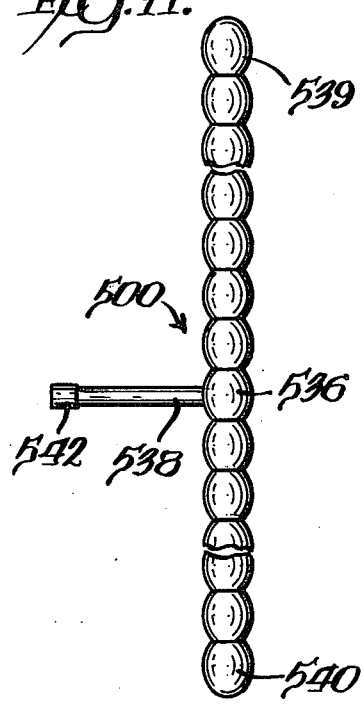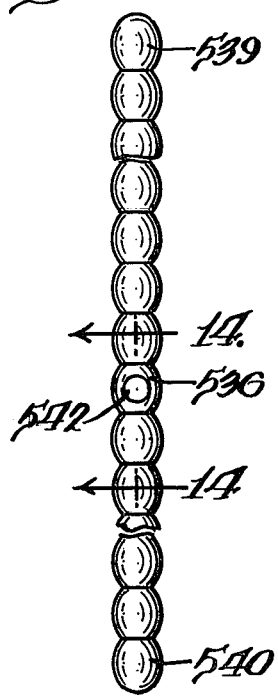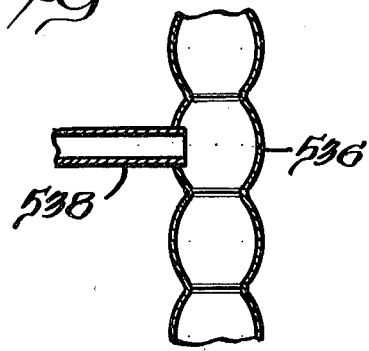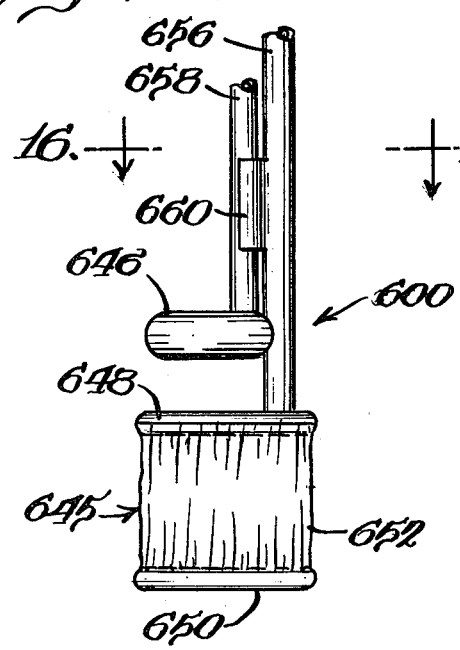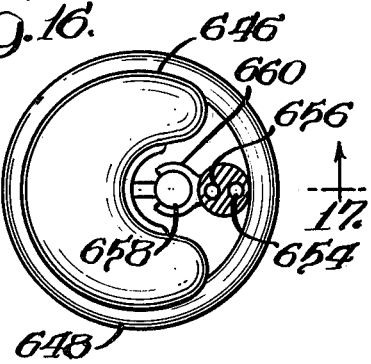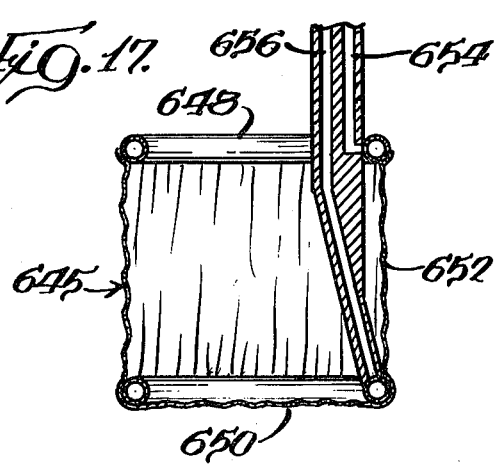

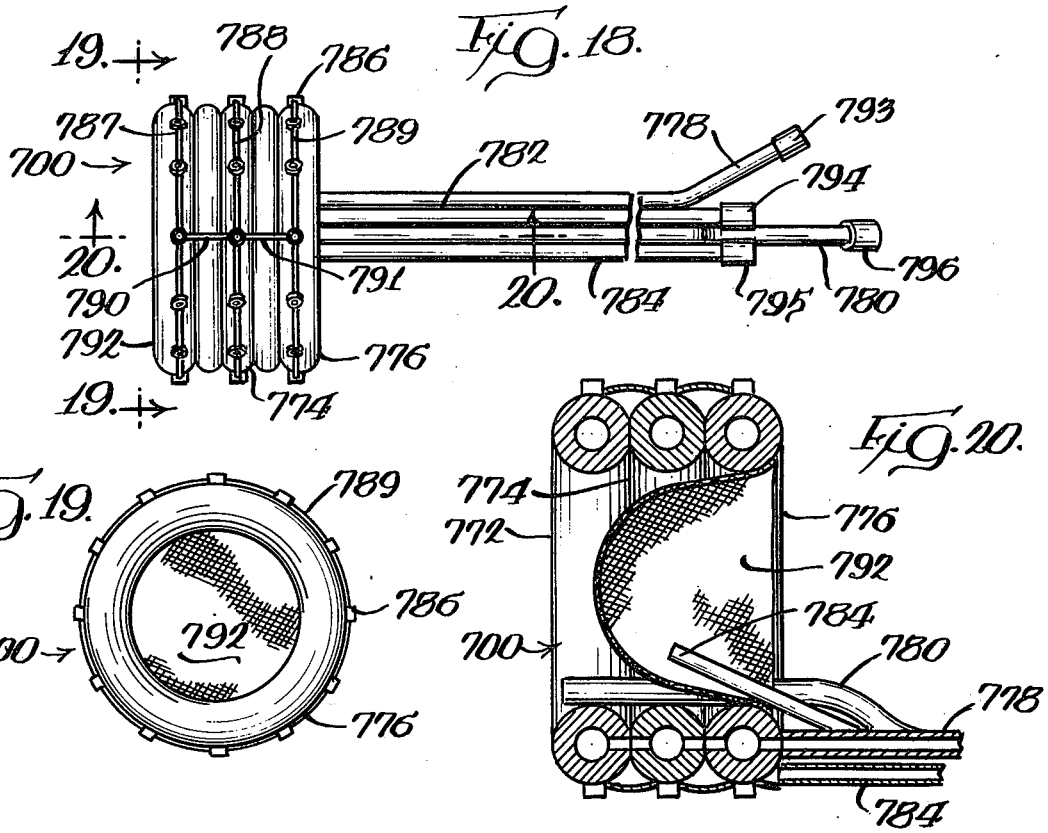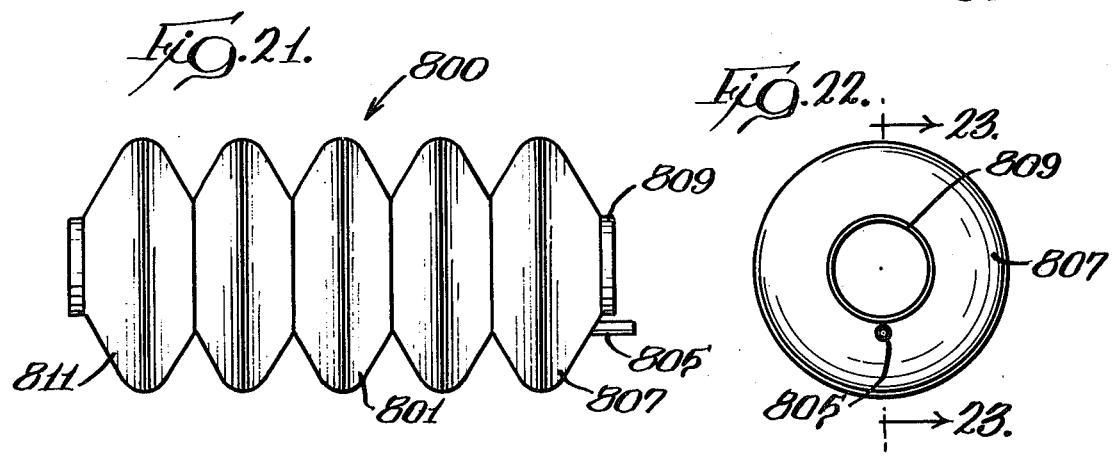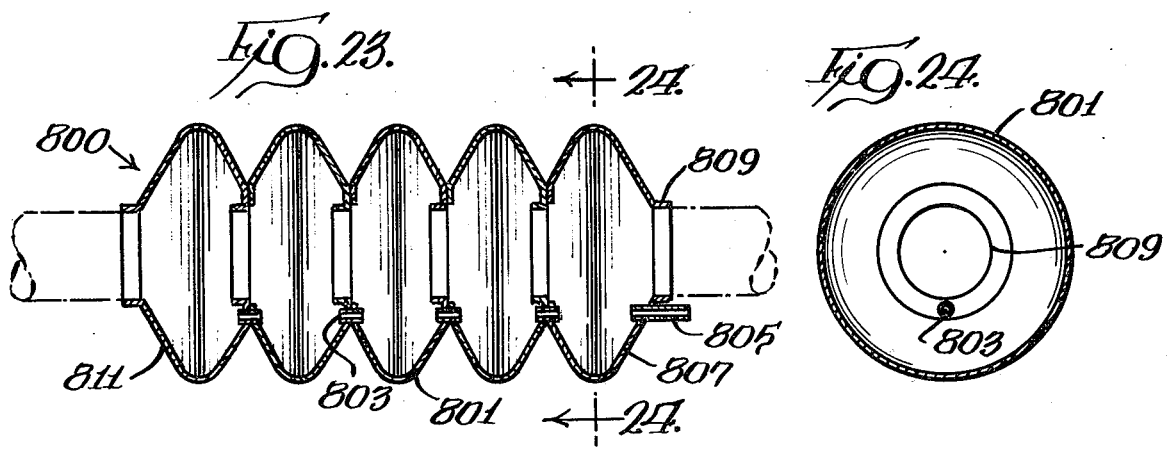

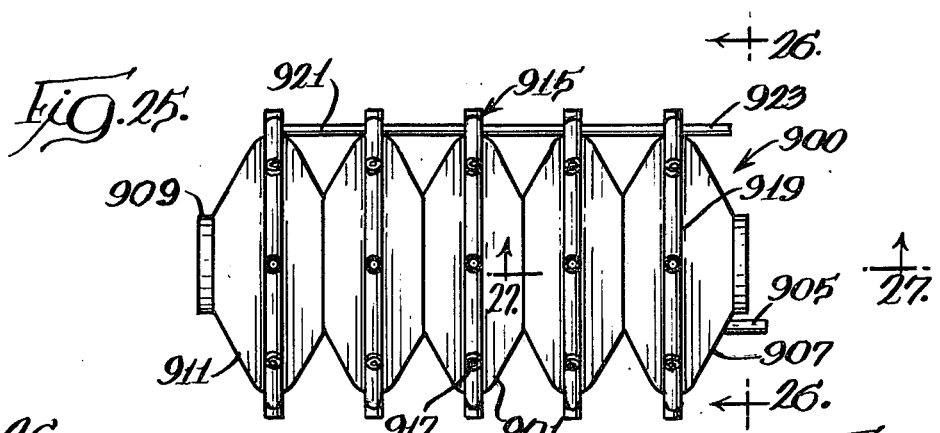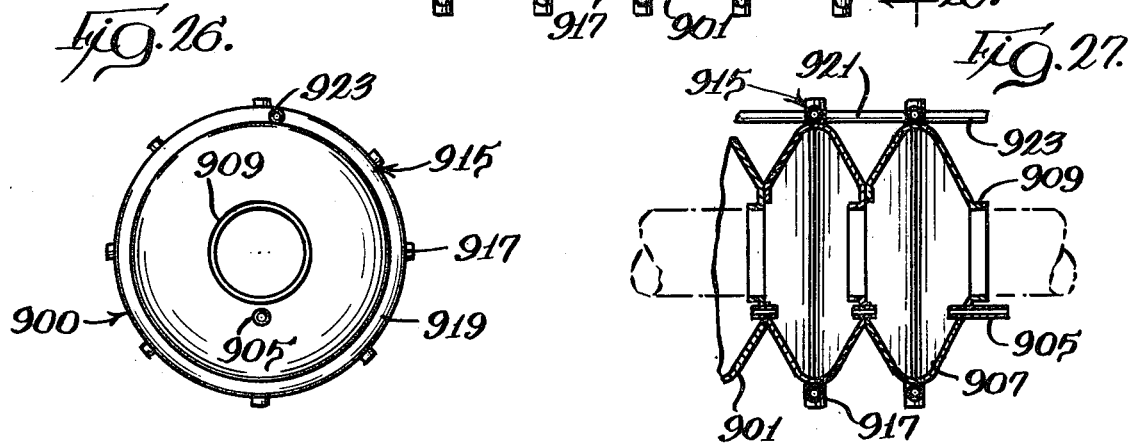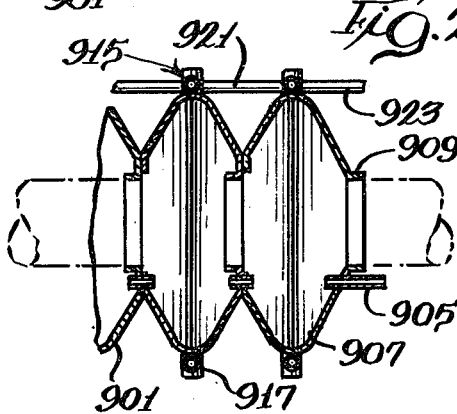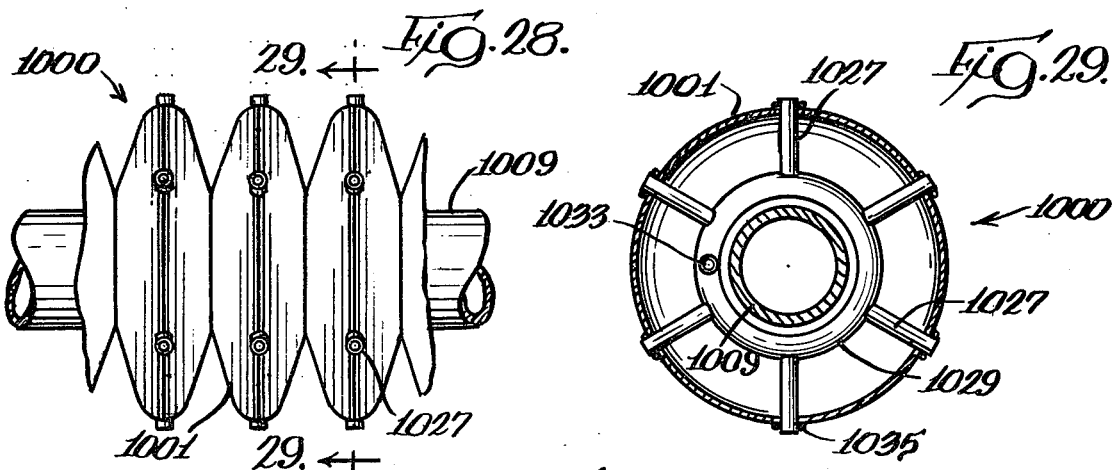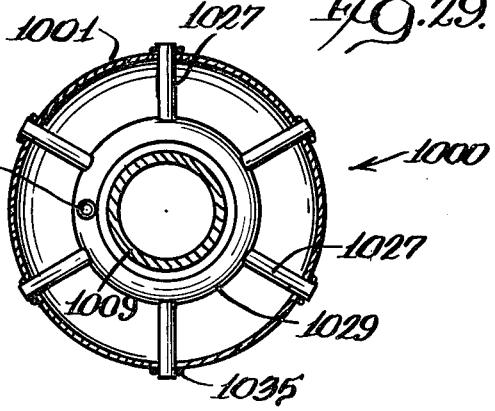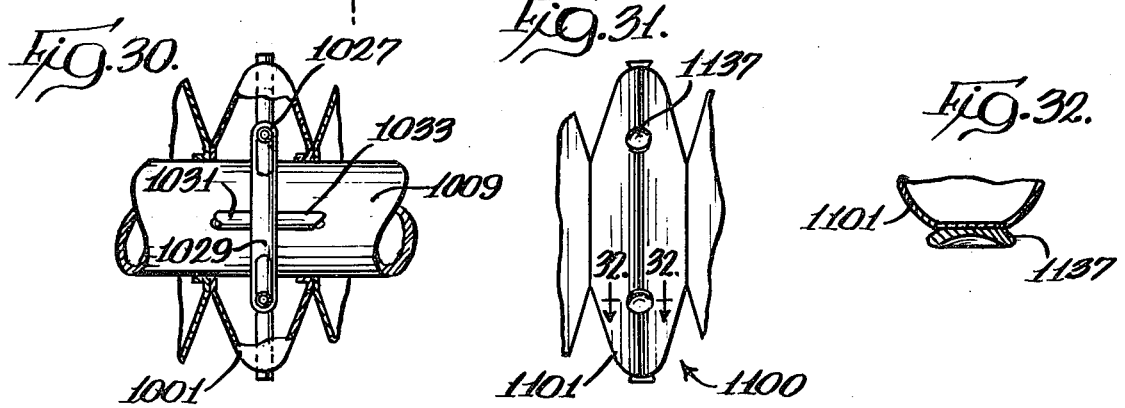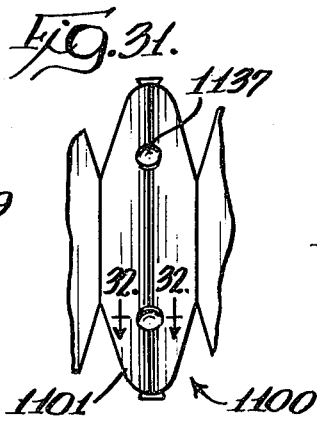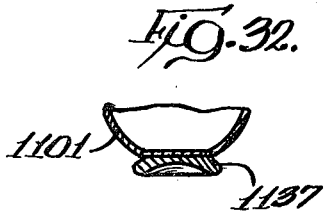

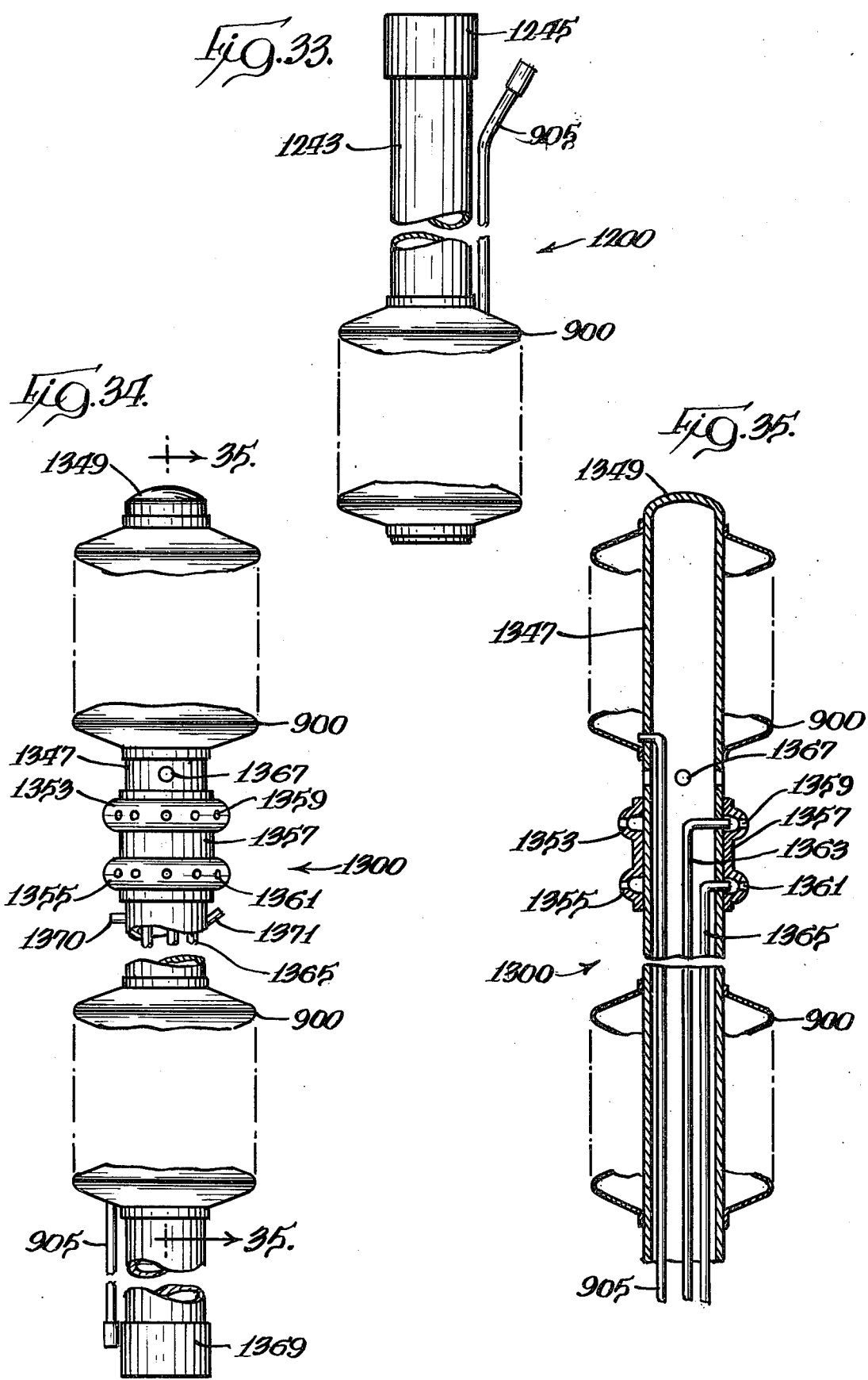

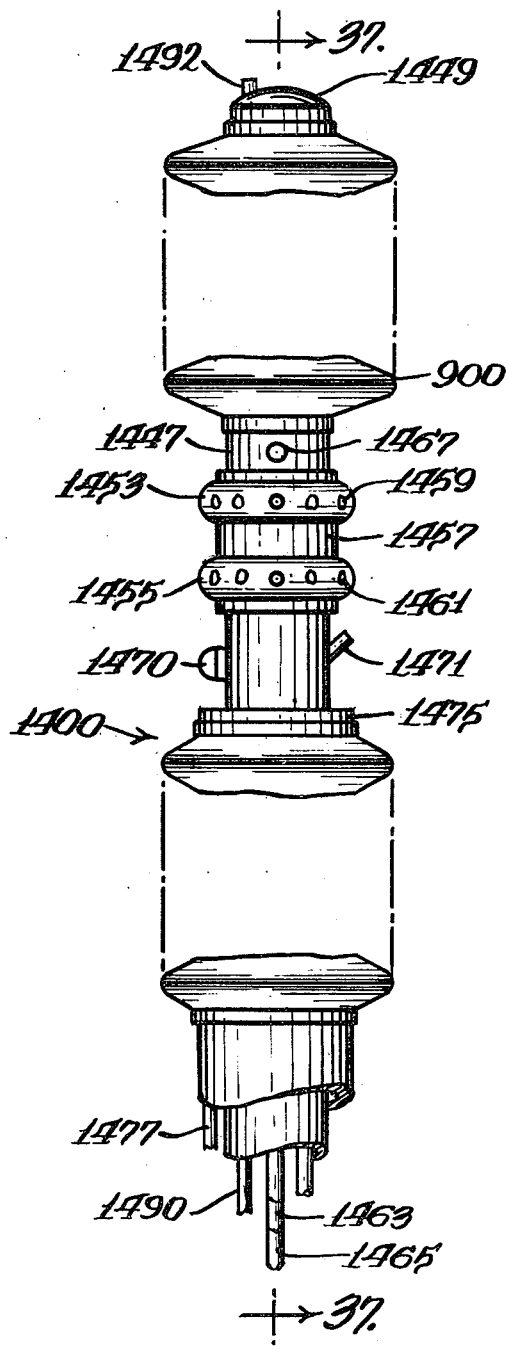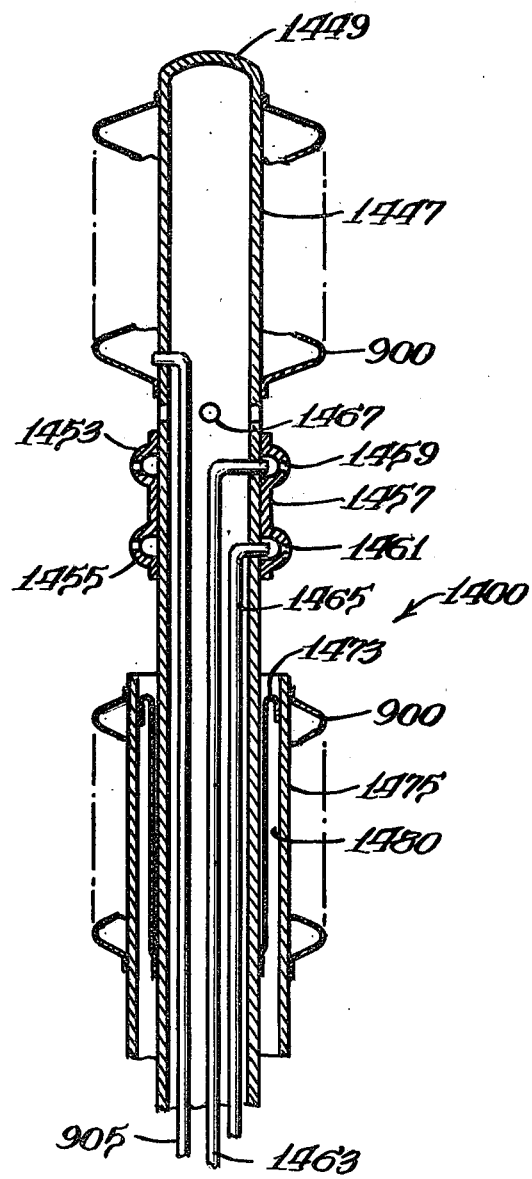

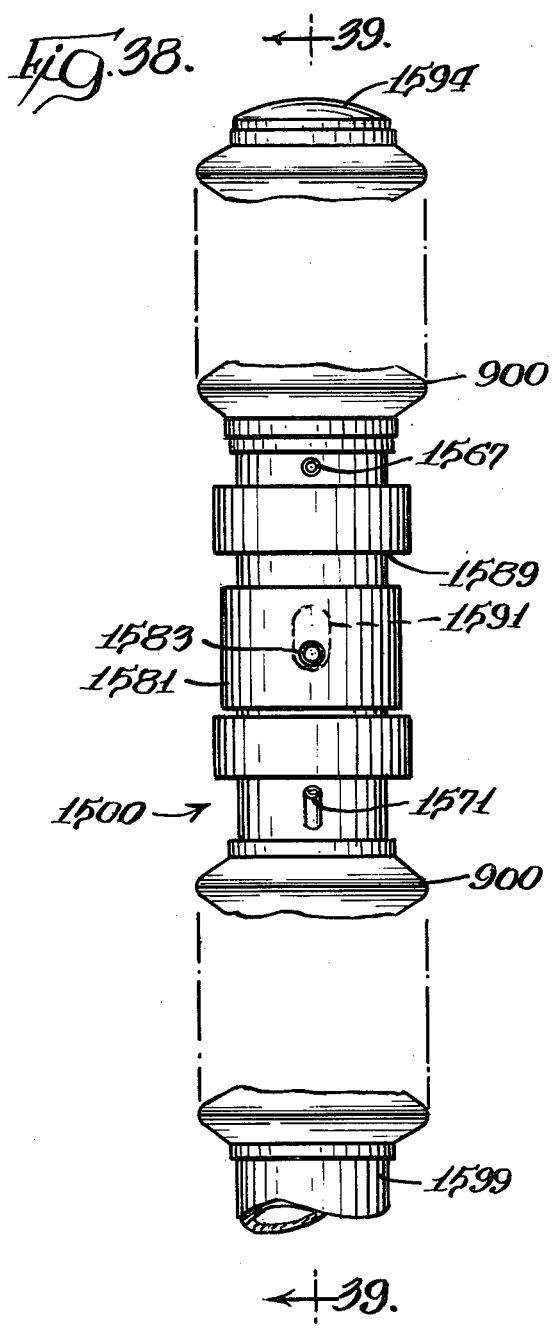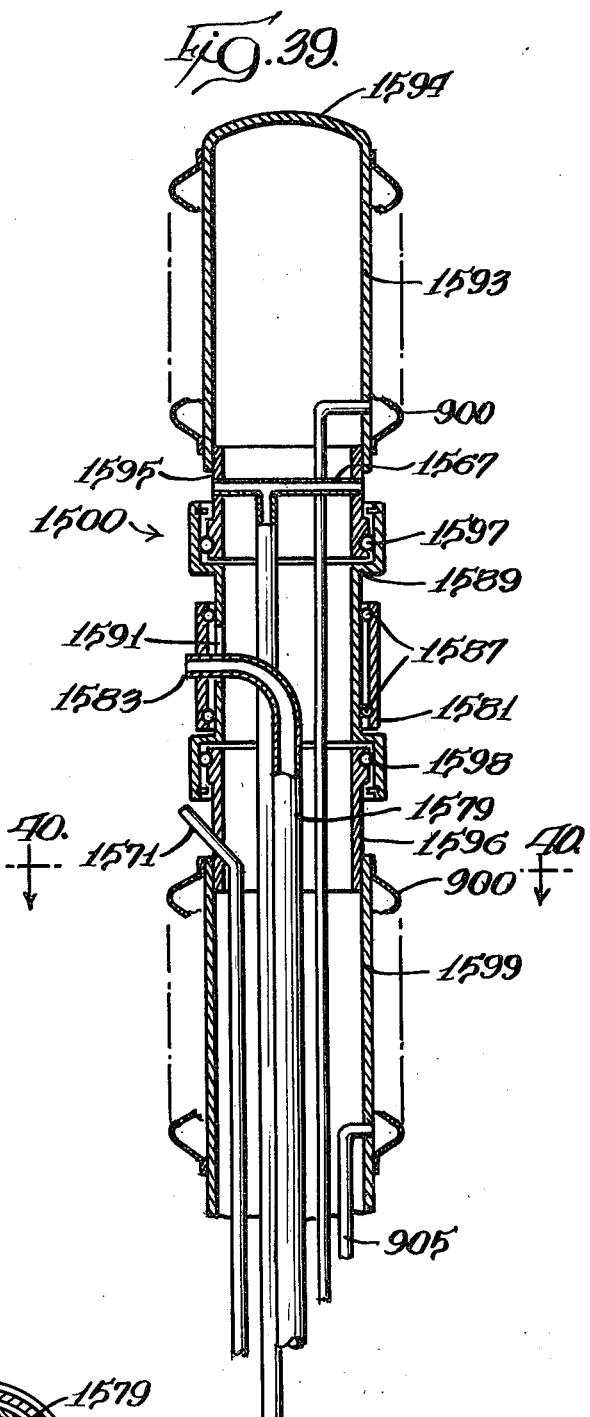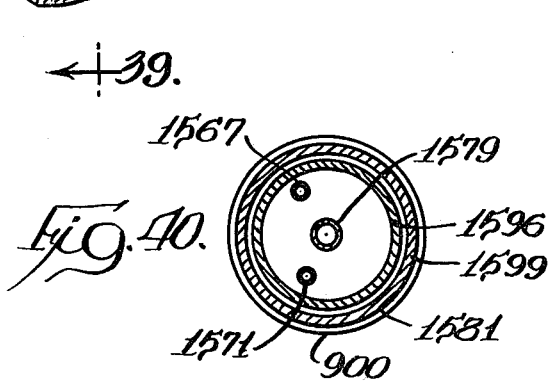

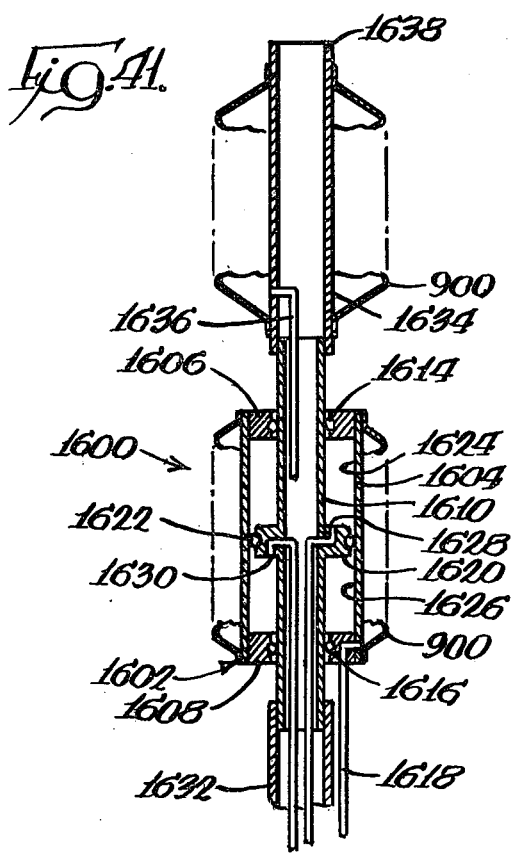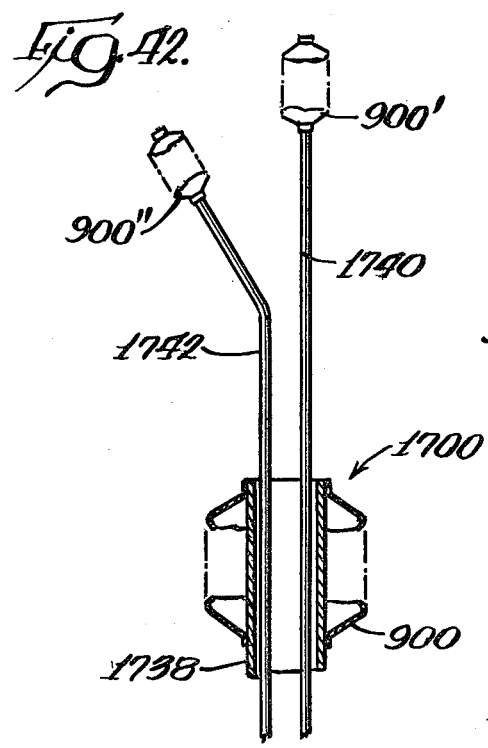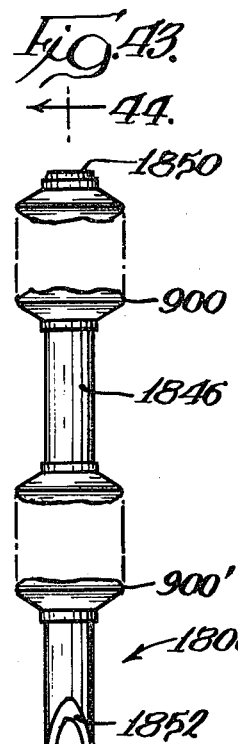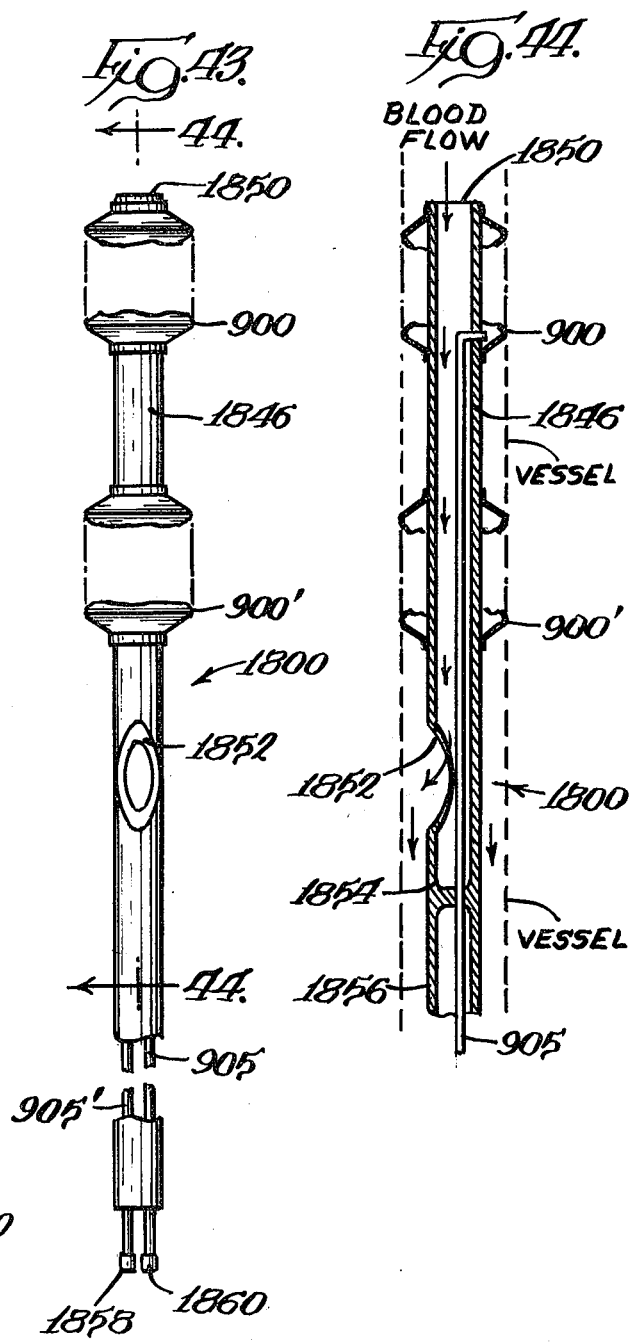

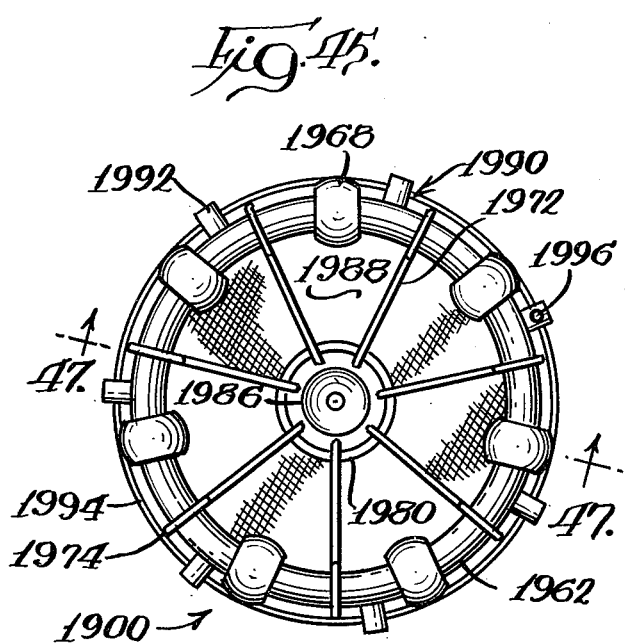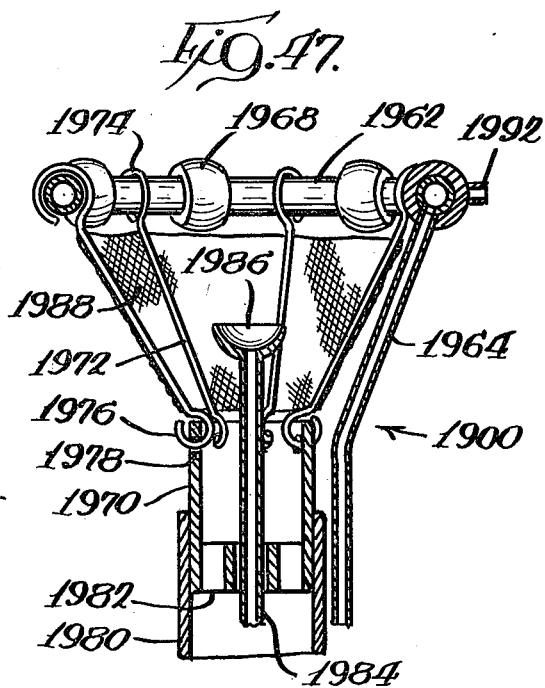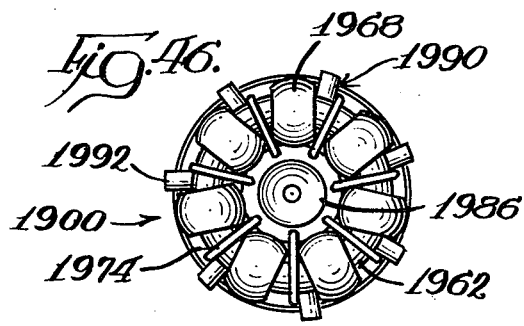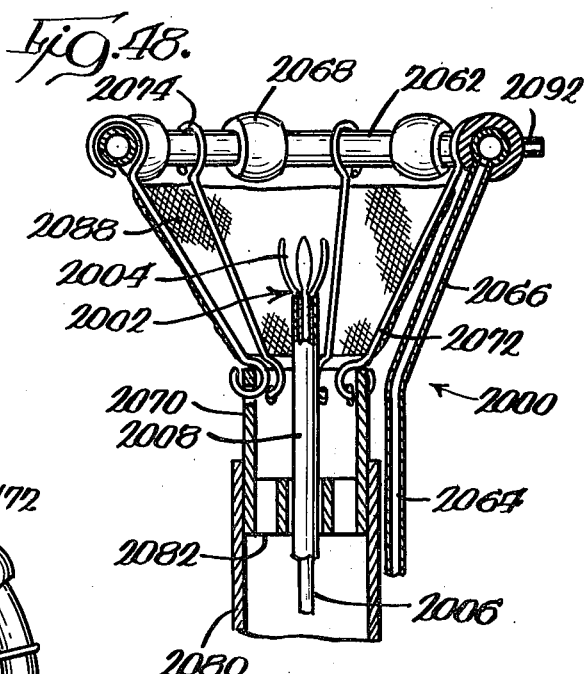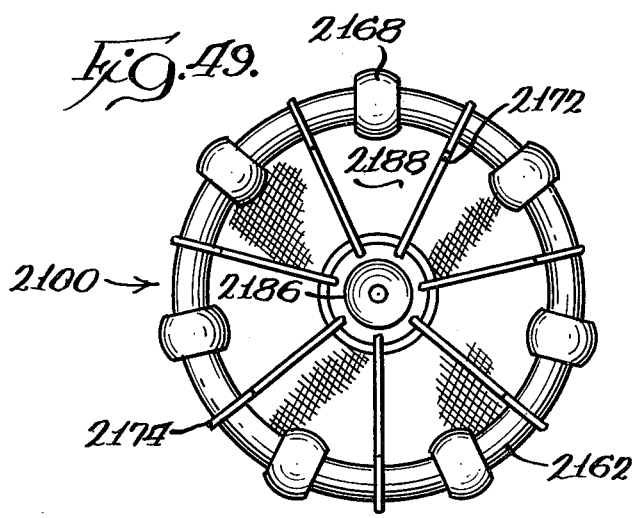

MULTI-PURPOSE MEDICAL DEVICES

TECHNICAL FIELD OF INVENTION

This invention relates to multi-purpose pneumatic and hydraulic devices for the medical and surgical profession.

BACKGROUND OF THE INVENTION

Patient care is of the utmost importance. Through simplification of existing techniques and providing a means to introduce new techniques, patient care can be greatly enhanced.

Over the years, a variety of new catheters, retractors, and other medical devices have been developed to enhance surgical techniques and provide for greater patient care. Typifying such catheters, retractors and other medical devices are those shown in U.S. Pat. Nos. 3,397,699, 3,490,457, 3,503,399, 3,528,869, 3,692,029, 3,815,608, 3,889,685, 3,889,686, 3,926,705, 3,982,544, 4,154,242, 4,154,244, 4,026,296, 4,144,884, 4,154,227, 4,154,243, 4,196,736, 4,202,332, 4,203,429, 4,203,430, 4,207,872, 4,207,898, 4,207,899, and 4,207,900. These catheters, retractors and other medical devices have met with varying degrees of success.

It is therefore desirable to provide improved multi-purpose medical devices to enhance surgical techniques and provide for greater patient care.

SUMMARY OF THE INVENTION

Multi-purpose medical devices are provided to facilitate and enhance surgical speed and accuracy for various surgical techniques and to improve diagnosis as well as to provide for greater patient care and recovery by minimizing trauma, infection and iatrogenic complications.

Each of the devices has a medical grade expandable balloon, sometimes referred to as a "fluid expansive envelope" or "membrane", that can be inflated with a fluid such as air, water, or another gas or liquid, to the size and pressure desired by the surgeon and subsequently deflated. Each of the devices also has a stabilizing means to enhance positioning, engagement and retention of the balloon in a desired lumen. The stabilizing structure can be in the form of an additional medical grade balloon or one or more vacuum responsive members, such as active or passive microsuckers.

As used throughout this application, the term "lumen" means a channel or cavity within a tubular organ of a patient. The lumen may be defined by a vessel, a tube or other organ of the human body.

In some of the embodiments, the medical grade balloon is in the form of a series of interconnected convoluted envelopes.

The medical device can also be equipped with a self-advancing assembly to sequentially advance and control movement of the medical device in a lumen and can include an optical system, such as a multi-lens system or fiberscope, to aid the physician in viewing the lumen.

The medical device can further have a vacuum retractor or crusher to remove secretions, feces and stones or other foreign objects from the lumen.

A more detailed explanation of the invention is provided in the following description and appended claims taken in conjunction with the accompanying drawings.

BRIEF DESCRIPTION OF THE DRAWINGS

FIG. 1 is a front view of a medical device embodying the present invention;

FIG. 2 is an end view of the medical device shown in FIG. 1;

FIG. 3 is a cross-sectional view taken substantially along line 3—3 of the medical device shown in FIG. 1;

FIG. 4 is an enlarged fragmentary cross-sectional view of the medical device taken substantially along 4—4 depicted in FIG. 1;

FIG. 5 is a front view of the medical device shown in FIG. 1 but in a deflated state;

FIG. 6 is an enlarged fragmentary cross-sectional view of another medical device;

FIG. 7 is a front view of still another medical device;

FIG. 8 is a top plan view of the medical device shown in FIG. 7;

FIG. 9 is an enlarged cross-sectional view taken substantially along 9—9 of the medical device shown in FIG. 8;

FIG. 10 is a cross-sectional longitudinal view of a further medical device;

FIG. 11 is a fragmentary front view of another medical device;

FIG. 12 is a side view of the medical device shown in FIG. 11;

FIG. 13 is an end view of the medical device shown in FIG. 11;

FIG. 14 is an enlarged fragmentary cross-sectional view taken substantially along line 14—14 of the medical device shown in FIG. 12;

FIG. 15 is a fragmentary front view of another medical device;

FIG. 16 is a cross-sectional view taken substantially along line 16—16 of the medical device shown in FIG. 15;

FIG. 17 is a cross-sectional view taken substantially along line 17—17 of the medical device shown in FIG. 16;

FIG. 18 is a perspective view of a further medical device;

FIG. 19 is an end view taken substantially along line 19—19 of the medical device shown in FIG. 18;

FIG. 20 is an enlarged fragmentary view taken substantially along line 20—20 of the medical device shown in FIG. 18;

FIG. 21 is a front view of another medical device;

FIG. 22 is an end view of the medical device shown in FIG. 21;

FIG. 23 is a cross-sectional view taken substantially along line 23—23 of the medical device shown in FIG. 22;

FIG. 24 is a cross-sectional view taken substantially along line 24—24 of the medical device shown in FIG. 23;

FIG. 25 is a front view of a further medical device;

FIG. 26 is an end view of the medical device shown in FIG. 25;

FIG. 27 is a fragmentary cross-sectional view of the medical device shown in FIG. 25;

FIG. 28 is a fragmentary perspective view of still another medical device;

FIG. 29 is a cross-sectional view taken substantially along line 29—29 of the medical device shown in FIG. 28;

FIG. 30 is a fragmentary view partly in section, of the medical device shown in FIG. 28;

FIG. 31 is a fragmentary front view of a further medical device;

FIG. 32 is an enlarged fragmentary cross-sectional view of a suction cup taken substantially along line 32—32 of the medical device shown in FIG. 31;

FIG. 33 is a fragmentary front view of another medical device;

FIG. 34 is a fragmentary front view of still another medical device;

FIG. 35 is a cross-sectional view taken substantially along line 35—35 of the medical device shown in FIG. 34;

FIG. 36 is a front view of another medical device;

FIG. 37 is a cross-sectional view taken substantially along line 37—37 of the medical device shown in FIG. 36;

FIG. 38 is a front view of still another medical device;

FIG. 39 is a cross-sectional view taken substantially along line 39—39 of the medical device shown in FIG. 38;

FIG. 40 is a cross-sectional view taken substantially along line 40—40 of the medical device shown in FIG. 39;

FIG. 41 is a longitudinal cross-sectional view of another medical device;

FIG. 42 is a fragmentary front view of another medical device shown partly in cross section;

FIG. 43 is a fragmentary front view of still another medical device;

FIG. 44 is a cross-sectional view taken substantially along line 44 of the medical device shown in FIG. 43;

FIG. 45 is a top plan view of another medical device;

FIG. 46 is a top plan view of the medical device shown in FIG. 45, but showing the device in a deflated state;

FIG. 47 is a cross-sectional view taken substantially along line 47—47 of the medical device shown in FIG. 45;

FIG. 48 is a fragmentary cross-sectional view of another medical device; and

FIG. 49 is a top plan view of a further medical device.

DETAILED DESCRIPTION OF THE PREFERRED EMBODIMENT

Referring now to FIGS. 1-5 of the drawings, a multi-purpose fluid responsive, lumen-engaging medical device or intralumen retractor 100 is provided for use in various medical and surgical procedures. Intralumen device 100 adds great precision and speed to various surgical techniques and minimizes trauma, infection and iatrogenic complications as well as other intraoperative and postoperative complications.

Intralumen device 100 has a pair of fluid expansive medical grade envelopes, balloons or expandable elastic membranes 102 and 104 which are spaced apart from each other and aligned in registration along a common axis. The second fluid expansive envelope 104 serves to enhance stabilization, positioning, engagement and retention of the first fluid expansive envelope 102 in a lumen of a tubular organ. Envelopes 102 and 104 have sockets 106 and 108 which provide openings that face each other and receive a T-shaped tube connector 110. Tube connector 110 has rigid Y-shaped Siamese tubes 112 and 114 defining fluid flow passageways and connected to envelopes 102 and 104, respectively, via sockets 106 and 108. Each of the envelopes 102 and 104 can be independently inflated or deflated to the desired size and pressure with a fluid, such as air, gas, water or other liquid, as desired by the surgeon, by connecting tubes 112 and 114 to a suitable edternal fluid pressure source such as a compressor or fluid pump, and regulating the fluid rate of pressure increase and pressure to be applied, e.g. by operating the compressor or the pump at a selected flow rate to produce a desired final pressure. In the illustrative embodiment, the outer ends of tubes 112 and 116 are provided with removable caps or fluid couplings 120 and 122.

In use, for example to perform an anastomosis, device 100 is inserted in the lumens to be joined in a collapsed state. Device 100 is then located at the desired anatomical position, and envelopes 102 and 104 are pneumatically or hydraulically inflated to the desired size and pressure to firmly engage against the internal surfaces of the walls of the lumens to be joined. After anastomosis is substantially completed, the envelopes 102 and 104 are deflated and device 100 is removed.

Device 100 is particularly useful in end-to-end anastomosis of lumens. Device 100 enhances the quality and precision of the surgical technique and increases the viability of the anastomosis.

Device 100 can be used for various procedures in the cardiovascular system, such as endarterectomy, valve replacement, arterial bypass, venous bypass, A-V shunts, coronary bypass, cannulation, resection of aneurysms and traumatic repair of vessels. Device 100 can also be used in various procedures for the gastrointestinal system, such as gastrectomy, small bowel resection, colectomy, ileostomy, colostomy, fistulectomy, esophangeal repair and pancreatobiliary tree repair. Device 100 is also useful in various procedures for genitourinary systems, such as ureter repair, re-implantation, bladder repair, urethra repair, urostomy, kidney transplants, salpingoplasty, hysterectomies, vaginal repair and fistulectomies.

One or both of the envelopes 102 and 104 can be equipped with vacuum suction members such as shown in FIGS. 25-30 to enhance the stabilization, positioning, engagement and holding attributes of the envelopes against the internal surfaces of the walls of the lumens.

The multi-purpose fluid reponsive, lumen-engaging medical device or intralumen retractor 200 shown in FIG. 6 is substantially similar to device 100 shown in FIGS. 1-5 except that a flexible inwardly tapered tube 202 with flared inlet and outlet nozzles 223 and 224 extends through the fluid expansive envelopes 202 and 204, as well as the T-shaped tube connector 210, to provide a blood flow passageway or conduit for passage of blood between the anastomosed lumens. For ease of understanding and of clarity, the parts and components of medical device 200 have been given part numbers similar to the parts and components of medical device 100 (FIGS. 1-5), except in the 200 series, such as envelope 204, tube connector 210, etc.

The multi-purpose fluid responsive, lumen-engaging medical device or intralumen retractor 300 shown in FIGS. 7-9 has many features and uses similar to the medical device 100 shown in FIGS. 1-5 and is particularly useful for end-to-side anastomosis of lumens. Device 300 has a primary, oblong, flexible, fluid expansive envelope, medical grade balloon or expandable elastic membrane 325 which is inflated or deflated with a fluid such as air, gas, water or other liquid to the size and pressure desired by the surgeon, via rigid tube and fluid flow passageway 326. A somewhat smaller medical grade flexible fluid expansive envelope, balloon or expandable elastic membrane 327 is securely attached at an angle of inclination to primary envelope 325. Inclined envelope 327 is separately inflatable and deflatable by another rigid tube and fluid flow passageway 328. Each of the tubes 326 and 328 have a removable cap or fluid coupling 329 or 330. As in the embodiments discussed above, the second envelope 327 serves to enhance the stabilization, positioning, engagement and retention of the first envelope 325 against the internal surfaces of the walls of its lumen. Both of the envelopes 325 and 327 can be equipped with suction stabilizing equipment as shown in FIGS. 25–30 for securely engaging the lumens under suction pressure.

The multi-purpose fluid responsive, lumen-engaging medical device or intralumen retractor 400 shown in FIG. 10 is similar to medical device 300 shown in FIGS. 7–9, except that an elongated rigid tube 431 with flared inlet and outlet nozzles 432 and 433 extends axially across the length of the primary envelope 425 and another rigid tube 434 with flared end nozzle 435 extends throughout the length of secondary envelope 427 and into primary envelope 425 where it is fluidly connected at an angle of inclination to primary tube 431 to provide blood flow passageways or conduits for continuous flow of blood between the anastomosed vessels. For ease of understanding and for clarity, the parts and components of the medical device 400 (FIG. 10) have been given part numbers similar to the parts and components of the medical device 300 (FIGS. 7–9) except in the 400 series, such as primary envelope 425, etc.

Referring now to FIGS. 11–14, a multi-purpose fluid responsive, lumen-engaging medical device or intralumen retractor 500 is provided with a series or array of aligned, interconnected convoluted fluid-expansive envelopes, medical grade balloons or expandable elastic membranes 536 which are positioned in fluid communication with each other. Fluid is introduced into or discharged from the center envelope 536 via a rigid tube and fluid flow passageway 538 (FIG. 11) to inflate or deflate envelopes 535 to the size and pressure desired by the surgeon. Tube 538 has a removable cap or fluid coupling 542. The uses and functional characteristics of medical device 500 (FIGS. 11–14) are similar to device 100 shown in FIGS. 1–5, except that the envelopes 535 are inflated or deflated with a single common tube 538.

The multi-purpose fluid responsive, lumen-engaging medical device or retractor 600 shown in FIGS. 15–17 has an expandable and collapsible cup or bucket 645 and a movable C-shaped, fluid-responsive pusher or elastic entrapment member 646. Pusher 646 cooperates with cup 645 to capture and entrap foreign objects in the esophagus, trachea, upper respiratory tree and elsewhere.

Cup 645 has upper and lower annular fluid-expansive envelopes, medical grade balloons or expandable, toroidal, elastic membranes 648 and 650 which are connected by an annular elastic wall or flexible membrane 652. Rigid tubes and fluid flow passageways 654 and 656 (FIG. 17) are connected to upper and lower envelopes 648 and 650, respectively, to inflate and deflate envelopes 648 and 650 to the size and pressure selected by the surgeon. Rigid tubes 654 and 656 extend axially upward from cup 645 and are integrally connected to each other.

Rigid pusher tube and fluid flow passageway 658 (FIG. 15) is connected and in fluid communication with pusher 46 to inflate and deflate pusher 646 to the size and pressure desired by the surgeon. Pusher tube 658 slides upon a mounting sleeve 660 which is securely attached to the periphery of tube 656 above pusher 646. Pusher tube 658 enables the surgeon to slidably advance and retract pusher 646 towards or away from the upper annular envelope 648 as desired. Pusher 646 and lower envelope 650 enhance stabilization, positioning, engagement and retention of upper envelope 648 against the inner surfaces of the walls of the lumen.

In use, pusher 646 and annular envelopes 648 and 650 are inflated to the desired size and pressure to wedge and entrap foreign objects in cup 645. Once the foreign object has been entrapped, envelopes 648 and 650 are deflated to collapse the flexible wall membrane 652 of cup 645 about the foreign object. Pusher 646 is then deflated. After the cup 645 has collapsed about the foreign object, the foreign object is removed by removing the retractor 600 from the patient.

Retractor 600 (FIG. 15) is particularly useful to remove foreign objects from the esophagus, trachea and upper respiratory tree. Advantageously, retractor 600 reduces the amount of time required to accomplish removal of foreign objects and minimizes the danger of a foreign body entering the trachea at the time of removal from the esophagus which sometimes occurs in conventional devices. Retractor 600 also effectively minimizes the necessity of follow-up surgical procedures because of failures of the initial surgical procedure.

In some circumstances, it may be desirable that the lower envelope 650 of retractor 600 be disc-shaped or circular rather than annular to provide a semi-flexible solid bottom for the cup.

Retractor 600 (FIG. 15) can also be equipped with a built-in lens system or other optical system or can be used in conjunction with roentgen fluoroscopy to visualize the foreign object area in question. Moreover, retractor 600 can be made radio-opaque to enhance roentgen fluoroscopy.

The multi-purpose fluid responsive, lumen-engaging medical device 700 shown in FIGS. 18–20 provides a temporary clot trapping and removing assembly for filtering blood clots and preventing embolism of clots to the lungs from the lower extremities. Clot trapping and removing assembly 700 serves as an alternative to the conventional Mobin-Uddin umbrella and the Greenfield filter, and is particularly advantageous in the prevention of pulmonary embolism.

Clot trapping and removing assembly 700 (FIGS. 18–20) has three annular, flexible, fluid expansive envelopes, medical grade balloons or elastic torroidal membranes 772, 774 and 776 which are concentrically and coaxially positioned with respect to each other. Intermediate envelope 774 is securely sandwiched between envelopes 772 and 776.

Rigid tube or fluid flow passageway 778 (FIG. 18) is connected in fluid communication to envelopes 772, 774 and 776, to inflate or deflate envelopes 772, 774 and 776 with air or other fluid as selected by the surgeon. Tubes 778, 780, 782 and 784 have detachable caps or fluid couplings 793, 794, 795 and 796, respectively. Tubes 780 and 782 are for pressure sensing and can also include pressure sensing devices (not shown) to sense the pressure of the lumen into which the clot trapping and removing assembly 700 is inserted.

Desirably, annular envelope 772, 774 and 776 (FIG. 18) are equipped with suction stabilizing members 786 (FIGS. 18 and 19) in the form of circumferentially spaced vacuum-responsive suction ports, which are sometimes referred to herein as "active suckers." Suction ports 786 are secured to and extend radially outwardly of annular envelopes 772, 774 and 776 which provide a vacuum annulus assembly. Suction ports 786 are also in fluid communication with each other by means of annular conduits 787, 788 and 789 (FIG. 18) and by transverse connecting conduits 790 and 791.

An axial rigid, vacuum connection tube 784 (FIGS. 18 and 20) is in fluid communication with annular conduit 789 and with a vacuum source to apply suction or negative pressure across the suction ports 786. The outer peripheral walls of annular envelope 772, 774 and 776 provide barriers which prevent the suction ports 786 from withdrawing the pressurizing fluid in the annular envelopes. In some circumstances, it may be desirable that the clot trapping and removing assembly have passive suckers in the form of suction cups such as shown in FIGS. 31 and 32 in addition to suctions ports 786.

In order to filter blood clots, a collapsible cup-shaped blood-clot filter or flexible net 792 (FIGS. 19 and 20) is attached to the periphery of rearward annular envelope 776. Filter 784 and annular envelopes 772, 774 and 776 together provide an elastic expandable frame. Stabilization, positioning, engagement and retention of filter 792 and intermediate envelope 774 are enhanced by suction ports 786 and annular envelopes 774 and 776. Tube 782 can also be used to clean filter 792 and decrease the morbidity of vena cava occlusion. Tubes 778, 780 and 782 (FIG. 18) are also helpful in providing information concerning the pressure of the vena cava and the effectiveness and condition of filter 792.

In use, clot trapping and removing assembly 700 is mounted on a self-advancing catheter and is inserted and positioned at the desired anatomical location on the vena cava.

After the clot trapping and removing assembly 700 has been anatomically positioned, the self-advancing catheter is withdrawn and annular envelopes 772, 774 and 776 are inflated via tube 778 to expand filter 792 to the desired size. Thereafter, suction pressure is applied to suction ports 786, via vacuum connection tube 784, to securely engage the vena cava under a suction pressure.

Filter 792 traps blood clots passing through the vena cava. After the blood clot has been entrapped in filter 792, the annular envelopes 772, 774 and 776 are deflated to collapse the filter 792 about the blood clot. The suction pressure is then released and the clot trapping and removing assembly 700 is removed with the clot from the patient. Once the clot trapping and removing assembly 700 has been removed from the patient, the annular envelopes can be inflated for access to the clot in the filter 792.

Referring now to FIGS. 21-24, the multi-purpose fluid responsive, lumen-engaging, convoluted medical device 800 is designed to sustain undesirable positional changes and to accommodate physiological changes of the lumen wall. To this end, convoluted medical device 800 has a series of interconnected convoluted, annular fluid expansive envelopes, medical grade balloons, or elastic torroidal membranes 801 which are positioned in alignment and in fluid communication with each other via a series of orifices or ports 803 (FIG. 23). A series of coaxial rigidification rings or collars 809 are positioned along the interior length of envelopes 801. A rigid tube and fluid flow passageway 805 is connected at one end to rearward envelope 807 and at its other end to a pneumatic or hydraulic pump (not shown).

In use, convoluted medical device 800 is secured to a tube or other suitable carrier and inserted into a lumen in its deflated state and moved to its desired anatomical position. Thereafter, the convoluted envelopes 801 are inflated with air, gas or other fluid to the desired size and pressure. During inflation, the fluid will sequentially and expansively flow from the rearward envelope 807 to the forward envelope 811.

The unique construction and arrangement of the convoluted envelopes 801 provides for increased surface area of contact and absorbs the peristaltic waves and rhythmic contractions of the lumen to effectively resist positional changes and accidental displacement of the convoluted medical device 800 once the medical device 800 has been placed in its desired anatomical position. Due to the multi-convoluted design of medical device 800, the convoluted medical device 800 is very resistant to peristalsis and other intralumen movements. The accommodation of the physiological changes of the lumen wall is accomplished by permitting the convoluted medical device 800 to stretch freely or passively along its length. When the first convoluted envelope 807 is compressed by the surrounding lumen, the pressurized air or other fluid in that envelope will flow to the adjacent and remaining convoluted envelopes 801 via orifices 803, causing the remaining envelopes to expand further which increases their holding power against the lumen. The displacement and expansion continues sequentially along the envelopes until the wave has passed. Therefore, with convoluted medical device 800, wave energy and spasms of the lumen are absorbed by the elastic convoluted envelopes. Stabilization, positioning and engagement of each of the convoluted envelopes is enhanced by the other envelopes.

Convoluted medical device 800 can hold a catheter or other instrument rigidly against the epithelial or intralumen surface of any hollow tube. Convoluted medical device 800 is particularly useful for gastrointestinal surgical procedures and forms the backbone of many of the other medical devices discussed below.

In some circumstances it may be useful as an alternative arrangement to interconnect the first and last convoluted envelopes 807 and 811, the second and next to last envelopes, and so forth, so that as a wave compresses the first convoluted envelope, its volume would be displaced to the last convoluted envelope because the convoluted envelope farthest from the wave would be at the relaxed portion of the lumen.

Referring now to FIGS. 25-27, the multi-purpose fluid responsive, lumen-engaging, convoluted medical device 900 shown in FIGS. 25-27 is similar to the convoluted medical device 800 shown in FIGS. 21-24, except that convoluted medical device 900 (FIG. 25-27) is equipped with a suction stabilizing assembly 915 with vacuum responsive suction ports 917, which are sometimes referred to as "active microsuckers." For ease of understanding and for clarity, the parts and components of convoluted medical device 900 (FIGS. 25-27) have been given part numbers similar to the parts and components of convoluted medical device 800 (FIGS. 21-24) except in the 900 series, such as convoluted envelopes 901, etc.

Suction ports 917 securely engage the lumen in question under a suction pressure to enhance stabilization, positioning, engagement and retention of convoluted envelopes 901. In the embodiment shown, suction ports 917 extend radially outward of convoluted envelopes 901 so as to circumscribe the convoluted envelopes.

The suction ports 917 on each convoluted envelope are circumferentially spaced from each other at equal intervals and are connected in fluid communication with each other by annular conduits and fluid flow passageways 919. The suction ports 917 of adjoining convoluted envelopes are connected in fluid communication with each other by longitudinal conduits 921. Suction ports 917 are preferably made of elastic tubular sections and are separated from the interior of the convoluted envelopes' outer wall.

A vacuum connection conduit 923 (FIG. 25) is connected at one end to suction ports 917 and at its opposite end to a suitable vacuum source to selectively draw a vacuum across suction ports 917. In the embodiment shown, vacuum connection conduit 923 is axially aligned with conduits 921.

Suction stabilizing assembly 915 assists in effectively minimizing positional changes and accidental displacement of the convoluted medical device 900 after the medical device has been placed at its desired anatomical position.

An alternative construction and arrangement of the suction stabilizing assembly of FIGS. 25-27 is shown in the multi-purpose fluid responsive, lumen-engaging, convoluted medical device 1000 shown in FIGS. 28-30. In embodiment of FIGS. 28-30, the suction stabilizing assembly has vacuum responsive suction ports or active microsuckers 1027 which extend radially outward from manifold rings 1029 (FIG. 29) positioned within the interior of the convoluted envelopes 1001.

Suction ports 1027 (FIG. 29) are connected in fluid communication with manifold ring 1029 and extend radially outward of convoluted envelopes 1001. The manifold rings 1029 are fluidly connected to each other by means of longitudinal conduits 1031 (FIG. 30) and are connected to a vacuum source, via a vacuum line 1033 (FIG. 30). Suction ports 1027 are bonded to envelopes 1001 or are provided with annular seals or gaskets 1035 (FIG. 29) that are mounted about suction ports 1027, against the outer peripheral walls of the convoluted envelopes 1001, to prevent leakage of fluid from envelopes 1001.

For ease of understanding and for clarity, the parts and components of convoluted medical device 1001 have been given part numbers similar to the parts and components of convoluted medical devices 800 (FIGS. 21-24) and 900 (FIGS. 25-27) except in the 1000 series.

The suction stabilizing assemblies in convoluted medical devices 900 (FIGS. 25-27) and 1000 (FIGS. 28-30) can also include one or more passive microsuckers or suction cups 1137, which extend from and are connected to the outer peripheral wall of the convoluted envelopes 1101, such as shown in the convoluted medical device 1100 of FIGS. 31-32.

Referring now to FIG. 33, the multi-purpose fluid responsive, lumen-engaging, convoluted medical device 1200 suitable for use as a colon catheter utilizes the elements of convoluted medical device 900 shown in FIGS. 25-27. Convoluted medical device 900 is mounted on a rigid elongated tube 1243 which extends axially through the convoluted medical device 900. A detachable cap or fluid coupling 1245 is located at the end of the rigid tube 1243.

In use, colon catheter 1200 (FIG. 33) is anatomically positioned above a diseased site in the large bowel of the patient in its deflated state with the aid of a colon scope or self-advancing assembly before the fecal liquid mass contained in the bowel becomes solid. Thereafter, the convoluted envelopes of the convoluted medical device 900 are inflated and a suction pressure is applied across the suction ports of convoluted medical device 900 to firmly grip the large bowel. When fully positioned, colon catheter 1200 diverts and drains the fecal liquid mass by gravity from the pathological site so as to allow the diseased segment of the colon sufficient time to heal sufficiently to withstand early surgery. A pneumatic valve (not shown) can regulate the fecal flow rate as desired by the physician.

Colon catheter 1200 (FIG. 33) aids and accelerates healing in instances that otherwise would require colon surgery. Colon catheter 1200 also provides the benefits of a temporary colostomy without the patient undergoing the danger and the expense of conventional surgery. Diseases of the colon such as diverticulitis that ruptured, persistent colon fistulas and severe forms of perianal abcess have before this invention undergone a two-step surgical procedure. The first step involves the resection of the diseased area and the concomitant diverting colostomy. The second step involves the closure of the temporary colostomy. With the new colon catheter 1200 of FIG. 33, a diverting colostomy is not necessary. Therefore the second and part of the first step are eliminated.

Colon catheter 1200 is particularly advantageous in decompression of the bowel distal to anastomosis and for gastrointestinal management of the large bowel.

Referring now to FIGS. 34 and 35, the multi-purpose fluid responsive, lumen-engaging, convoluted medical device, panendoscope or panmulticatheter 1300 of FIGS. 34-35 has a pair of convoluted medical devices 900, of the type shown in FIGS. 25-27, mounted on a rigid elongated tube 1347 so that the rigid tube 1347 extends through the length of the interior of the convoluted medical devices 900.

Rigid tube 1347 (FIG. 34) has a close rounded end or front wall 1349. One of the convoluted medical devices 900 is mounted on the rigid tube 1347 adjacent the front wall 1349. The other convoluted medical device 900 is mounted on the rigid tube 1347 rearwardly of the first convoluted medical device 900. The bottom of rigid tube 1347 has a detachable cap or fluid coupling 1369 (FIG. 34), as do the other tubes.

Vacuum or pressure responsive sparge rings 1353 and 1355 (FIG. 34) are circumferentially mounted upon the outer periphery of rigid tube 1347 between convoluted suction devices 900. The sparge rings 1353 and 1355 are integrally connected by a collar 1357 and are each constructed with a series of circumferentially spaced suction-apertures or ports 1359 and 1361.

A tube 1363 (FIG. 35), which is bent at right angles and extends axially along the interior of rigid tube 1347, communicates with upper sparge ring 1353. Another tube 1365, which is oriented in a similar manner, communicates with the lower sparge ring 1355. Tubes 1363 and 1365 are connected to vacuum or pressure sources (not shown).

Rigid tube 1347 (FIGS. 34 and 35) has at least one inlet opening or aperture 1367 that communicates with the space defined by the lumen and convoluted medical devices 900.

Panendoscope 1300 (FIG. 34) also has a multi-lens optical system 1370 and fiberscope 1371. At the present time, the choice of instruments and proper technique are important considerations in the performance of endoscopy. The fiberoscope of panendoscope 1300 permits the entire gastrointestinal tract to be directly visualized without missing small lesions or lesions of jejunum, ileum and therefore enables the physician to study the anatomy and pathophysiology of the gastrointestinal tract with greater detail. Previously, the study of jejunum and ileum could only be studied by roentgen methods. The fiberoscope of panendoscope 1300, however, obviates roentgen methods and the presence of expert endoscopists to perform endoscopy.

Panendoscope 1300 (FIGS. 34–35) can be used for diagnostic radiology, gastroenterology and vascular surgery. Panendoscope 1300 is particularly useful to immobilize a portion of the lumen and aid the physician to study the subject portion of the lumen in detail through endoscopic or radiological means. Panendoscope 1300 refines and extends existing endoscopic procedures to improve the diagnosis and clinical management of gastrointestinal disorders. Panendoscope 1300 also decreases patient discomfort by minimizing endoscopy time.

Panendoscope device 1300 (FIGS. 34 and 35) can be used in the gastrointestinal system for detailed study of the entire gastrointestinal tract under direct visualization, biopsy of pathoanatomical lesions, direct visualization of jejunum and ileum, visualization of all fistulas and diverticula irrespective of size and location in the gastrointestinal tract, release of acute bowel obstructions, resolution of mechanical ileus, intesusseption and volvulus, tamponade of active bleeding ulcers and of varicose veins of esophagus, gradual dilatation of stenotic or atrophic parts of the gastrointestinal tract and double air contrast studies of the gastrointestinal tract. Panendoscope 1300 is also useful for studying different lumens in detail, for visualizing fistulas anywhere in the genitourinary system and for facilitating advancement of catheters and other instruments during intralumen propagation.

Among the many other advantages of panendoscope 1300 (FIGS. 34 and 35) are its ability to immobilize and completely isolate the desired portion of the lumen in question. Panendoscope 1300 also permits easy catheterization of fistulas and ducts of any lumen to decrease the amount of time required for endoscopy. Moreoever, pandendoscope 1300 minimizes the necessity for a second endoscopy and permits dilatation of a segment of any lumen.

Referring now to FIGS. 36 and 37, the multi-purpose fluid responsive, lumen engaging, convoluted medical device, panendoscope or panmulticatheter 1400 of FIGS. 36 and 37, is substantially similar in construction and use to the panendoscope 1300 of FIGS. 34 and 35, except that panendoscope 1400 (FIGS. 36 and 37) has a fluid-responsive annular diaphragm sealed by elastic membrane 1473 (FIG. 37) that is operatively positioned between rigid tube 1447 and a hollow shaft member or collar 1475 that is secured to the inner annular surface of the lower convoluted medical device 900. For ease of understanding and for clarity, the parts and components of panendoscope 1400 (FIGS. 36 and 37) have been given part numbers similar to the parts and components of panendoscope 1300 (FIGS. 34 and 35) except in the 1400 series, such as sparge rings 1453 and 1455, etc.

Diaphragm 1473 (FIG. 37) serves as a seal to facilitate the pressurization of the annular space 1480 between rigid tube 1447 and collar 1475. The panendoscope 1400 is advanced in the lumen by sequencing pressurization of annular space 1480 and inflating and deflating convoluted medical devices 900. The injection of air or other fluid into annular space sealed by membrane 1473 will cause a forward thrust and advancement of panendoscope 1400.

Panendoscope 1400 can be provided with lens system or fiberscope 1490 with lens 1492 extending beyond front wall 1449 to provide viewing during endoscopy. This system can also be used on panendoscope 1300. This system permits an endoscopist to easily view the entire gastrointestinal tract and study its anatomy and pathophysiology under great detail. Even small lesions can be visualized.

Referring now to FIGS. 38–40, the multi-purpose fluid responsive, lumen-engaging, convoluted medical device, panendoscope, fiberoduodenoscope, or panmulticatheter 1500 of FIGS. 38–40 is generally similar to the panendoscope 1300 of FIGS. 34 and 35 except that in lieu of sparge rings, fiberoduodenoscope 1500 has a vacuum responsive retracter or suction tube or guide tube 1579 (FIG. 39), which is slidably positioned within a rotatable collar assembly 1581. For ease of understanding and for clarity, the parts and components of fiberoduodenoscope 1500 (FIGS. 38–40) have been given part numbers similar to the parts and components of panendoscope 1300 (FIGS. 34 and 35) except in the 1500 series.

As shown in FIG. 39, suction tube 1579 extends axially along the interior of fiberoduodenoscope 1500 and is bent at a rounded right angle so that its distal end or tip 1583 extends radially outwardly of collar assembly 1581. The lower end of suction tube 1579 can be connected to a vacuum source (not shown) to selectively apply a suction or negative pressure across the tip 1583 of suction tube 1579.

Collar assembly 1581 (FIG. 38) has a round opening through which tube tip 1583 is retained. Collar assembly 1581 rotates upon ball bearings 1587 (FIG. 39) located between the collar assembly and an I-shaped annular detainer 1589. The I-shaped annular detainer 1589 has an elongated detainer slot to permit forward and rearward (up and down) movement of the tip 1583 of suction tube 1579.

In the fiberoduodenoscope 1500 of FIG. 39, an upper, forward tube section 1593 has a closed rounded end or top 1594 which supportingly carries an upper convoluted medical device 900 such as the convoluted medical device shown in FIGS. 25–27. Connected to the bottom of the upper forward tube section 1593 is a tubular bypass section 1595. The I-shaped detainer 1589 circumscribes the lower part of the tubular bypass section 1595 and is connected thereto forming a fluid-tight seal by means of O-ring 1597. A T-shaped bypass tube 1567 is operatively connected to the tubular bypass section.

The lower portion of the I-shaped detainer 1589 circumscribes and is connected to the upper portion of a tubular fiberscope-supporting section 1596 via O-ring 1598. Connected to the bottom of the tubular fiberscope-supporting section 1596 is a lower, rearward tube section 1599. The lower, rearward tube section 1599 carries a lower convoluted medical device 900 which is structurally similar to the upper convoluted medical device.

A fiberscope 1571 extends through an opening in the tubular fiberscope-supporting section 1596. Fiberscope 1571 permits the physician to visually examine the anatomical site as the fiberscope is advanced. Upon reaching the desired site, a fiberscope or probe is inserted into guide tube 1579 and extended beyond tip 1583. By axial and rotational movement of collar 1581, the entire anatomical site is available for study. The fiberscope is also helpful to visually examine the duodenopancreatobiliary tree, lumen to lumen fistula and lumen to skin fistula.

In use, the fiberoduodenoscope is positioned at the desired anatomical location and the convoluted medical devices 900 are inflated to the size and pressure desired by the surgeon. A vacuum pressure is then drawn across the convoluted medical devices 900. Afterwards, tube 1579 is rotated until its tip 1583 is positioned against or closely adjacent the lesion, stone or foreign object sought to be removed or studied. Rotation of tube 1579 will cause rotation of collar assembly 1581. After the tube 1579 has been positioned at the desired anatomical location, the vacuum source, fiberscope, or probe is activated. After the procedure has been completed, the convoluted medical devices 900 are deflated and the vacuum pressure across the convoluted medical devices is withdrawn. Fiberoduodenoscope 1500 is then removed from the patient while holding the lesion, foreign body, or stone with the suction tube under suction pressure. The suction pressure can then be released to remove the object from suction tip 1583.

Fiberoduodenoscope 1500 is useful for endoscopic pancreatography, cholangiography, duodenoscopy and upper gastrointestinal endoscopy. Fiberoduodenoscope 1500 increases the success rate of pancreatography to almost 100 percent with greater efficiency of surgical time. Fiberoduodenoscope 1500 also decreases patient discomfort and minimizes the necessity of a second endoscopy. Fiberoduodenoscope 1500 is particularly helpful in aiding (ERCP) in the diagnosis and clinical treatment of duodenopancreatobiliary diseases. Fiberoduodenoscope 1500 can also incorporate the self advancing features and a fiberscope as described for panendoscope 1400.

Referring now to FIG. 41, the multi-purpose fluid responsive, lumen-engaging, convoluted medical device or catheter 1600 of FIG. 41 provides a self-advancing carrier to propel various devices through a lumen. To this end, catheter 1600 has an automatic sequencer including a fluid-responsive collar assembly 1602. Collar assembly 1602 has an elongated tubular collar 1604 upon which is circumferentially mounted a convoluted medical device 900, such as the convoluted medical device shown in FIGS. 25-27. Annular end walls 1606 and 1608 close the ends of collar 1604 about a rigid tube 1610 via seals or O-rings 1614 and 1616.

An annular propulsion member 1620 located between annular walls 1606 and 1608 integrally extends radially outwardly from tube 1610 and is fluidly sealed to the inner surface of collar 1604 by a seal or O-ring 1622. Annular propulsion member 1620 provides a wall-like barrier which divides and partitions collar assembly 1602 into a forward propulsion chamber 1624 and a rearward propulsion chamber 1626. A generally Z-shaped conduit and fluid flow passageway 1628 extends through annular propulsion member 1620 and communicates with forward propulsion chamber 1624 to inject air or other fluid into forward propulsion chamber 1624 and propel catheter 1600 in a forwardly direction. A reversely bent conduit and fluid flow passageway 1630 extends through annular propulsion member 1620 and communicates with rearward propulsion member 1626 to inject air or other fluid into the rearward propulsion chamber 1626 and propel catheter 1600 in a rearward direction.

Rigid tube 1610 is connected at its lower end to rearward tube 1632 and at its upper end to upper tube 1634. An upper convoluted medical device 900, which is similar in construction to lower convoluted medical device, except it has a smaller inside diameter, is circumferentially mounted upon upper tube 1634. Upper convoluted medical device 900 is inflated and deflated to the size and pressure desired by the surgeon via a conduit 1636 which extends through upper tube 1634. The lower convoluted medical device 900 is inflated and deflated to the size and pressure desired by the surgeon via a conduit 1618 which extends through the rearward end wall 1608 and collar 1604. Desirably, an instrument or other medical device, such as a fiberscope or a stone removing catheter as shown in FIGS. 45-47 can be mounted upon the top 1638 of upper tube 1634.

In use, air or other fluid is injected into forward propulsion chamber 1624 via conduit 1628 to propel catheter 1600 forwardly along the lumen. Air or other fluid is injected into the rearward propulsion chamber 1626 via conduit 1630 to propel catheter 1600 rearwardly along the lumen. The propulsion velocity of the catheter 1600 is a function of the inflation pressure and flow rate. The propulsion velocity can also be increased by deflating the rearward chamber 1626 while inflating the forward chamber 1624 and vice versa. In this manner, the surgeon can sequentially control movment of the catheter 1600 to and from the desired anatomical sites.

Referring now to FIG. 42, the multi-purpose fluid responsive, lumen-engaging, medical device or panendoscope 1700 of FIG. 42 has a rigid tube 1738 upon which is circumferentially mounted a primary convoluted medical device 900, such as the convoluted medical device shown in FIGS. 25-27. Extending through tube 1738 is an elongated conduit 1740 and an obtusely bent conduit 1742. Conduits 1740 and 1742 can have any configuration and rigidity needed to accomodate a desired application. A smaller convoluted medical device 900', which is structurally similar to but smaller than primary convoluted medical device 900, is circumferentially mounted upon the end of elongated conduit 1740. Another convoluted medical device 900'', which is similar to convoluted medical device 900', is circumferentially mounted upon the end of obtusely bent conduit 1742. A fiberscope can also be included within conduits 1740 and 1742 to permit viewing of the fallopian tubes.

In use, panendoscope 1700 (FIG. 42) is inserted and positioned in its collapsed state in the fallopian-uterine junction. When in place, the convoluted medical devices 900, 900' and 900'' are inflated to the size and pressure desired by the gynecologist and a selected suction pressure is drawn across the convoluted medical device to grasp the fallopian-uterine junction and occlude the continuation of the uterus to the fallopian tubes. An endoscope is then inserted into panendoscope 1700 to perform the required endoscopy. Panendoscope 1700 can also be positioned in the vagina-cervical junction to occlude the continuation of the vagina-cervical junction.

In the past, endoscopy of the uterus has been accomplished with the use of certain liquids or carbon dioxide. Panendoscope 1700 effectively eliminates complications and disadvantages of both conventional liquids and carbon dioxide. Desirably, the gynecologist can use carbon dioxide to inflate or expand the convoluted medical devices 900, 900' and 900'' and can effectively evaluate and treat diseases relating to the uterus with panendoscope 1700.

The primary purpose of panendoscope 1700 is to aid gynecologists with endoscopic and radiological procedures. Among the many advantages of panendoscope 1700 is its ability to provide for ease of diagnosis of any lesion or anomaly of uterus, biopsy, lysis of adhesions, interuterine device (IUD) withdrawal, extension of endoscopy to occlude the fallopian tubes and eliminate existing adverse effects of expansion media.

Referring now to the multi-purpose fluid responsive, lumen-engaging, medical bypass device 1800 shown in FIGS. 43 and 44, bypass device 1800 has a rigid elongated open ended tube 1846 upon which is circumferentially mounted a pair of convoluted medical devices 900 and 900' of the type shown in FIGS. 25-27. The convoluted medical devices are inflated and deflated via conduits 905 and 905', respectively, which have detachable caps or fluid flow couplings 1858 and 1860 (FIG. 43).

Tube 1846 is open ended at its top to define an access opening or inlet 1850 for ingress of blood. Tube 1846 also has an inwardly tapered elliptical discharge outlet 1852, which is elongated in the axial direction and is located below the lower convoluted medical device 900' for egress of blood. A barrier and internal wall 1854 is positioned below outlet 1852 to prevent passage of blood to lower chamber 1856.

In use, an incision is made proximally or distally to the injured or ruptured site of a vessel, and bypass device 1800 is inserted in the vessel, so that the ruptured site is isolated between the upper and lower convoluted medical devices 900 and 900'. The convoluted medical devices are then inflated to the size and pressure desired by the surgeon and a selected suction pressure is drawn across the convoluted medical devices until the bypass device 1800 is securely positioned in place. Bypass device serves to direct the patient's blood past the injured or ruptured site by directing the blood into tube 1846 through inlet 1850 and out through outlet 1852 thereby bypassing the injured or ruptured site. Bypass device 1800 is particularly useful for cardiovascular surgical emergencies.

While the convoluted medical device of FIGS. 25-27 can be used in conjunction with the multi-purpose fluid responsive, lumen-engaging, medical devices 1200-1900 of FIGS. 33-44, it is to be understood that other convoluted medical devices such as those shown in FIGS. 28-32 can be used in lieu thereof.

Referring now to FIGS. 45-47, the multi-purpose fluid responsive, lumen-engaging, medical device or stone removing catheter 1900 of FIGS. 45-47 remove stones, feces (stools) and other foreign objects from a lumen, duct or upper and lower respiratory tree with the aid of an endoscope. To this end, stone removing catheter 1900 has an annular fluid-expansive medical-grade envelope, balloon, expandable torroidal-shaped elastic membrane, circular tube or ring 1962 into which air or other fluid is injected or removed through an obtusely bent, semi-rigid tube and fluid flow passageway 1964 that is connected to a compressor or fluid pump (not shown). Annular envelope 1962 extends through a series of circumferentially spaced truckles or rollers 1968.

Positioned between truckles 1968 (FIG. 47) and pivotally mounted upon annular envelope 1962 are upper C-shaped hooks 1974 (FIG. 47) which are integrally connected to upwardly diverging rigidifying ribs 1972. Rigidifying ribs 1972 are integrally connected to lower C-shaped hooks 1976 which pass through apertures or openings 1978 in a collar or tubular section 1970 so that the rigidifying ribs are pivotally connected to the collar or tubular section. Rigidifying ribs are positioned along the internal surface of a truncated flexible elastic membrane 1988 to rigidify and assist in sustaining the shape of the truncated membrane.

An annular bushing 1982 (FIG. 47) is mounted within the interior of collar 1970. An elongated rigid tube 1980 is telescopically connected to the exterior of collar 1970. Extending through annular bushing 1982 is a vacuum retractor 1984. Vacuum retractor 1984 has a cup-shaped, concave suction nozzle or head 1986 which is circumferentially surrounded by truncated membrane 1988. Truncated membrane 1988 cooperates with ribs 1972 to form a collapsible cup which collapses about, covers and encloses suction head 1986 when envelope 1962 is deflated.

In order to enhance stabilization, positioning, engagement and retention of envelope 1962, stone removing catheter 1900 has a suction stabilizing vacuum assembly 1990 (FIGS. 45 and 46) with circumferentially spaced suction stabilizing members or ports 1992 that extend radially outwardly of annular envelope 1962. An annular conduit 1994 (FIG. 45) is connected in fluid communication with ports 1992. A vacuum connection line or conduit 1996 (FIG. 45) is connected at one end to annular conduit 1994 and at its other end to a vacuum source (not shown) so that the surgeon can apply the desired suction pressure across ports 1992.

In use, stone removing catheter 1900 is inserted in the collapsed state into the lumen or duct in question. A fiberscope can be inserted through tube 1980 parallel to retractor 1984 to allow viewing while catheter 1900 is being located and used. After the stone removing catheter 1900 has been located at the desired anatomical position, annular envelope 1962 is inflated with air or other fluid to size and pressure desired by the surgeon. Inflation of envelope 1962 will assist in dislodging stones, feces and foreign bodies from the lumen. A suction pressure is then applied to suction ports 1992 until the suction ports firmly engage the lumen. After the stone removing catheter 1900 has been secured against the lumen, a suction pressure is applied to the suction head 1986 of vacuum retractor 1984 to draw in and hold under suction pressure any loose stones, feces and foreign bodies in the lumen. Annular envelope 1962 is thereafter deflated and the suction across ports 1992, but not suction head 1986, released so that truncated membrane 1988 will collapse, encapsulate, cover and entrap the foreign body upon suction head 1986 to enable the stone removing catheter 1900 to be removed from the patient. After the stone removing catheter is removed, envelope 1962 is inflated to permit access to the suction head 1986. The suction pressure across suction head 1986 is then released and the foreign object removed.

In contrast to conventional devices where only stones that are embedded into the pelvic portion of the ureter are accessible, stone removing catheter 1900 (FIGS. 45-47) can remove stones regardless of their anatomical site.

Stone removing catheter 1900 (FIG. 45-47) is particularly useful in removing stones from the biliary tree as well as removal of fecal material in severely constipated patients. Stone removing catheter 1900 is also helpful in removing stones from the entire length of the ureter as well as the urinary bladder and urethra. Stone removing catheter 1900 helps minimize additional surgery and aids the physician in the treatment of urinary tract and biliary tree lithiasis as well as severe constipation. Stone removing catheter 1900 also reduces the need for further surgery in the genitourinary system and biliary tree lithiasis, improves the clinical management of lithiasis patients and expedites lithiasis removing procedures.

Referring to FIG. 48, the multi-purpose fluid responsive, lumen-engaging, medical device or stone-removing catheter 2000 of FIG. 48, is substantially similar to the stone removing catheter 1900 of FIGS. 45–47, except that the stone removing catheter 2000 of FIG. 48 has a mechanical impact crusher 2002 in lieu of a vacuum retractor 1984. Mechanical impact crusher 2002 has claw-like pincers 2004 which can be expanded and retracted by pulling and pushing, respectively, a wire rod 2006 that is attached to the pincers. Wire rod 2006 extends through a rigid tube 2008.

In use, pincers 2004 squeeze, crush and break up the stone, feces or other foreign body in the lumen into smaller pieces which can then be grasped by the pincers for easy and comfortable removal from the patient. For ease of understanding and for clarity, the parts and components of the stone removing catheter 2000 (FIG. 48) have been given part numbers similar to the parts and components of catheter 1900 (FIGS. 45–47) except in the 2000 series, such as annular envelope 2062, ports 2092, etc.

The multi-purpose fluid responsive, lumen-engaging, medical device or stone-removing catheter 2100 shown in FIG. 49 is similar to the stone removing catheter 1900 shown in FIGS. 45–47, except that the suction stabilizing vacuum assembly has been omitted. For ease of understanding and for clarity, the parts and components of the stone removing catheter 2100 (FIG. 49) have been given part numbers similar to the parts and components of the stone removing catheter 1900 (FIGS. 45–47), except in the 2100 series, such as annular envelope 2162, etc.

Although embodiments of the invention have been shown and described, it is to be understood that various modifications and substitutions, as well as rearrangement of parts, can be made by those skilled in the art without departing from the novel spirit and scope of this invention.

What is claimed is:

1. A medical device, comprising:
   fluid expansive, convoluted annular envelope means for positioning in a lumen of a tubular organ;
   fluid flow passageway means communicating with said fluid expansive, convoluted annular envelope means with a fluid;
   tube means extending at least partially through said fluid expansive, convoluted annular envelope means; and
   suction stabilizing means operatively associated with and extending outwardly from said fluid expansive, convoluted annular envelope means for engaging the wall defining said lumen and retaining said envelope means under suction pressure at a desired anatomical site.

2. A medical device in accordance with claim 1 wherein said suction stabilizing means include a plurality of vacuum responsive suction ports positioned in fluid communication with each other about said fluid expansive, convoluted annular envelope means.

3. A medical device in accordance with claim 1 wherein said suction stabilizing means includes a plurality of suction cups positioned about said fluid expansive, convoluted annular envelope means.

4. A medical device in accordance with claim 1 including vacuum responsive sparge ring means mounted upon said tube means.

5. A medical device in accordance with claim 1 further including optical means operatively associated with said tube means.

6. A medical device in accordance with claim 1 wherein said tube means includes blood-flow passageway means.

7. A medical device in accordance with claim 1 further including rotatable collar means positioned about said tube means and suction tube means extending radially outwardly of said rotatable collar means for removing stones and other foreign matter from said lumen under suction pressure.

8. A medical device in accordance with claim 1 further including fluid responsive annular diaphragm means operatively positioned between said fluid expansive envelope means and said tube means for sequentially controlling movement of said medical device along said lumen.

9. A medical device in accordance with claim 1 further including fluid responsive collar means operatively associated with said tube means for providing an automatic sequencer to sequentially control movement of said medical device along said lumen, said fluid responsive collar means defining a forward propulsion chamber and a rearward propulsion chamber, first conduit means for injecting fluid into said forward propulsion chamber to propel said medical device generally forwardly along said lumen, and second conduit means for injecting fluid into said rearward propulsion chamber to propel said medical device generally rearwardly along said lumen.

* * * * *

UNITED STATES PATENT AND TRADEMARK OFFICE
CERTIFICATE OF CORRECTION

PATENT NO. : 4,447,227
DATED : May 8, 1984
INVENTOR(S) : CONSTANTINE A. KOTSANIS

It is certified that error appears in the above-identified patent and that said Letters Patent is hereby corrected as shown below:

Claim 1, column 1, line 53, after "means" insert

--for selectively inflating and deflating said fluid expansive convoluted annular envelope means-- .

Signed and Sealed this

Ninth Day of October 1984

[SEAL]

Attest:

*Attesting Officer*

GERALD J. MOSSINGHOFF

*Commissioner of Patents and Trademarks*